(12) United States Patent
Tachikawa et al.

(10) Patent No.: US 10,039,937 B2
(45) Date of Patent: Aug. 7, 2018

(54) CHARGED-PARTICLE BEAM THERAPY APPARATUS AND METHOD FOR CONTROLLING CHARGED-PARTICLE BEAM THERAPY APPARATUS

(71) Applicant: SUMITOMO HEAVY INDUSTRIES, LTD., Tokyo (JP)

(72) Inventors: Toshiki Tachikawa, Niihama (JP); Toru Asaba, Niihama (JP); Masanori Tachibana, Niihama (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 299 days.

(21) Appl. No.: 14/661,480

(22) Filed: Mar. 18, 2015

(65) Prior Publication Data

US 2015/0265855 A1  Sep. 24, 2015

(30) Foreign Application Priority Data

Mar. 24, 2014  (JP) ................................. 2014-060020

(51) Int. Cl.
*A61N 5/10* (2006.01)

(52) U.S. Cl.
CPC .......... *A61N 5/1048* (2013.01); *A61N 5/1043* (2013.01); *A61N 2005/1087* (2013.01)

(58) Field of Classification Search
CPC ................ A61N 5/1043; A61N 5/1048; A61N 2005/1087
See application file for complete search history.

(56) References Cited

U.S. PATENT DOCUMENTS

| 2011/0049372 A1* | 3/2011 | Iseki | A61N 5/1043 |
| | | | 250/362 |
| 2014/0005463 A1* | 1/2014 | Jongen | A61N 5/1037 |
| | | | 600/1 |

FOREIGN PATENT DOCUMENTS

| JP | 52-113591 A | 9/1977 |
| JP | 2011-050585 A | 3/2011 |
| JP | 2011-130859 A | 7/2011 |
| JP | 2011-194196 A | 10/2011 |
| JP | 2011-239841 A | 12/2011 |

OTHER PUBLICATIONS

Japanese Patent Office, Office Action corresponding to Application No. 2014-060020, dated Jul. 11, 2017.

* cited by examiner

*Primary Examiner* — Thaddeus Cox
(74) *Attorney, Agent, or Firm* — Squire Patton Boggs (US) LLP

(57) ABSTRACT

A charged-particle beam therapy apparatus includes: an accelerator configured to accelerate a charged particle and emit a charged-particle beam; an irradiation unit configured to irradiate an irradiated body with the charged-particle beam using a scanning method; and a control unit. The control unit stores a control pattern of the apparatus during one treatment. An irradiation interruption time for which the irradiation of the irradiated body with the charged-particle beam by the irradiation unit is interrupted and an irradiation time for which the irradiation unit irradiates the irradiated body with the charged-particle beam are set in the control pattern. The sum of the irradiation interruption times during one treatment is set to be shorter than the sum of the irradiation times during one treatment.

3 Claims, 13 Drawing Sheets

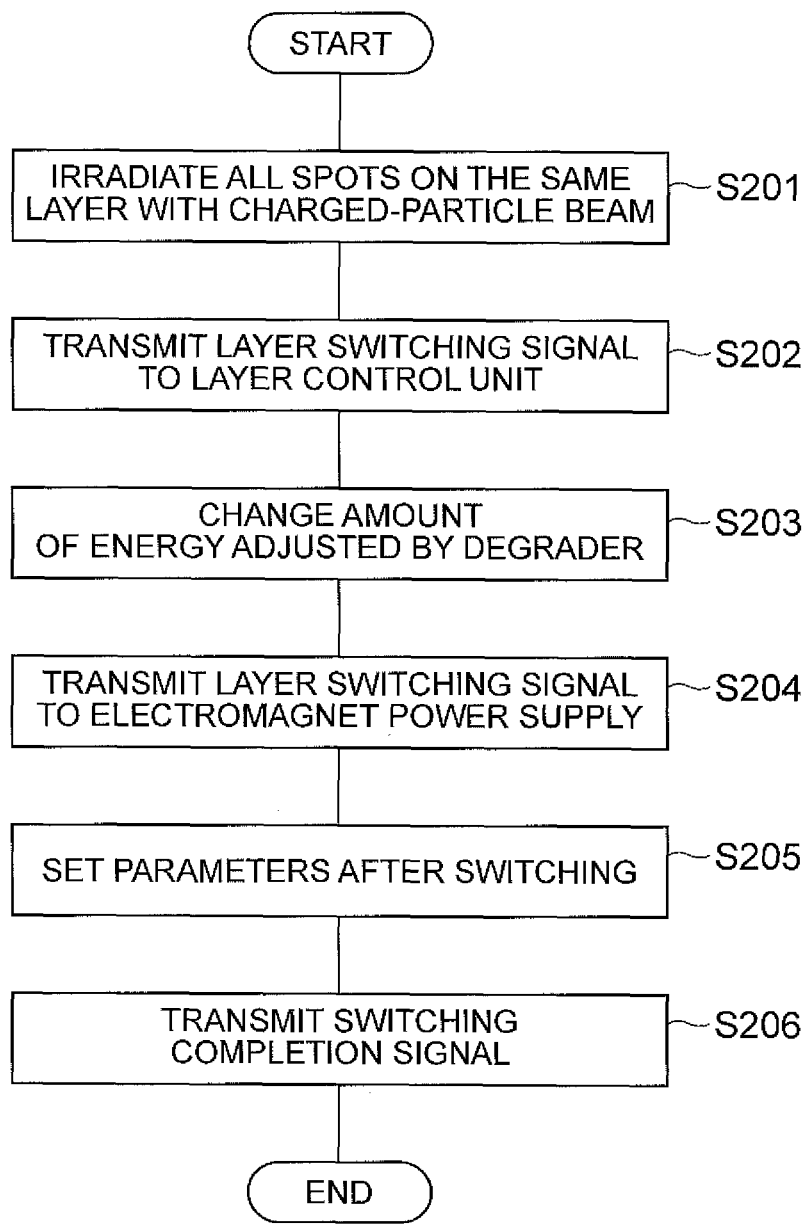

CHARGED-PARTICLE BEAM THERAPY APPARATUS AND METHOD FOR CONTROLLING CHARGED-PARTICLE BEAM THERAPY APPARATUS

RELATED APPLICATIONS

Priority is claimed to Japanese Patent Application No. 2014-060020, filed Mar. 24, 2014, the entire content of which is incorporated herein by reference.

BACKGROUND

Technical Field

The present invention relates to a charged-particle beam therapy apparatus and a method for controlling a charged-particle beam therapy apparatus.

Description of Related Art

In recent years, a scanning-type charged-particle beam therapy apparatus has been known as a charged-particle beam therapy apparatus which irradiates an irradiated body with a charged-particle beam and performs treatment. This charged-particle beam therapy apparatus irradiates one layer set in the irradiated body with the charged-particle beam according to a predetermined scanning pattern, changes the energy of the charged-particle beam when the irradiation of the one layer with the charged-particle beam is completed, and irradiates the next layer with the charged-particle beam. This charged-particle beam therapy apparatus controls the radiation of the charged-particle beam according to the movement of the irradiated body caused by, for example, the breathing of the patient.

SUMMARY

According to an embodiment of the invention, there is provided a charged-particle beam therapy apparatus including: an accelerator configured to accelerate a charged particle and emit a charged-particle beam; an irradiation unit configured to irradiate an irradiated body with the charged-particle beam using a scanning method; and a control unit. The control unit stores a control pattern of the apparatus during one treatment. In the control pattern, an irradiation interruption time for which the irradiation of the irradiated body with the charged-particle beam by the irradiation unit is interrupted and an irradiation time for which the irradiation unit irradiates the irradiated body with the charged-particle beam are set. The sum of the irradiation interruption times during one treatment is set to be shorter than the sum of the irradiation times during one treatment.

According to another embodiment of the invention, there is provided a method for controlling a charged-particle beam therapy apparatus including an irradiation unit which irradiates an irradiated body with a charged-particle beam using a scanning method and a control unit. The method includes: causing the control unit to control the irradiation of the irradiated body with the charged-particle beam on the basis of a control pattern of the apparatus during one treatment; setting an irradiation interruption time for which the irradiation of the irradiated body with the charged-particle beam by the irradiation unit is interrupted and an irradiation time for which the irradiation unit irradiates the irradiated body with the charged-particle beam in the control pattern; and setting the sum of the irradiation interruption times during one treatment to be shorter than the sum of the irradiation times during one treatment.

BRIEF DESCRIPTION OF THE DRAWINGS

FIG. 4 is a flowchart illustrating the content of a layer switching process;

DETAILED DESCRIPTION

Figure 1:
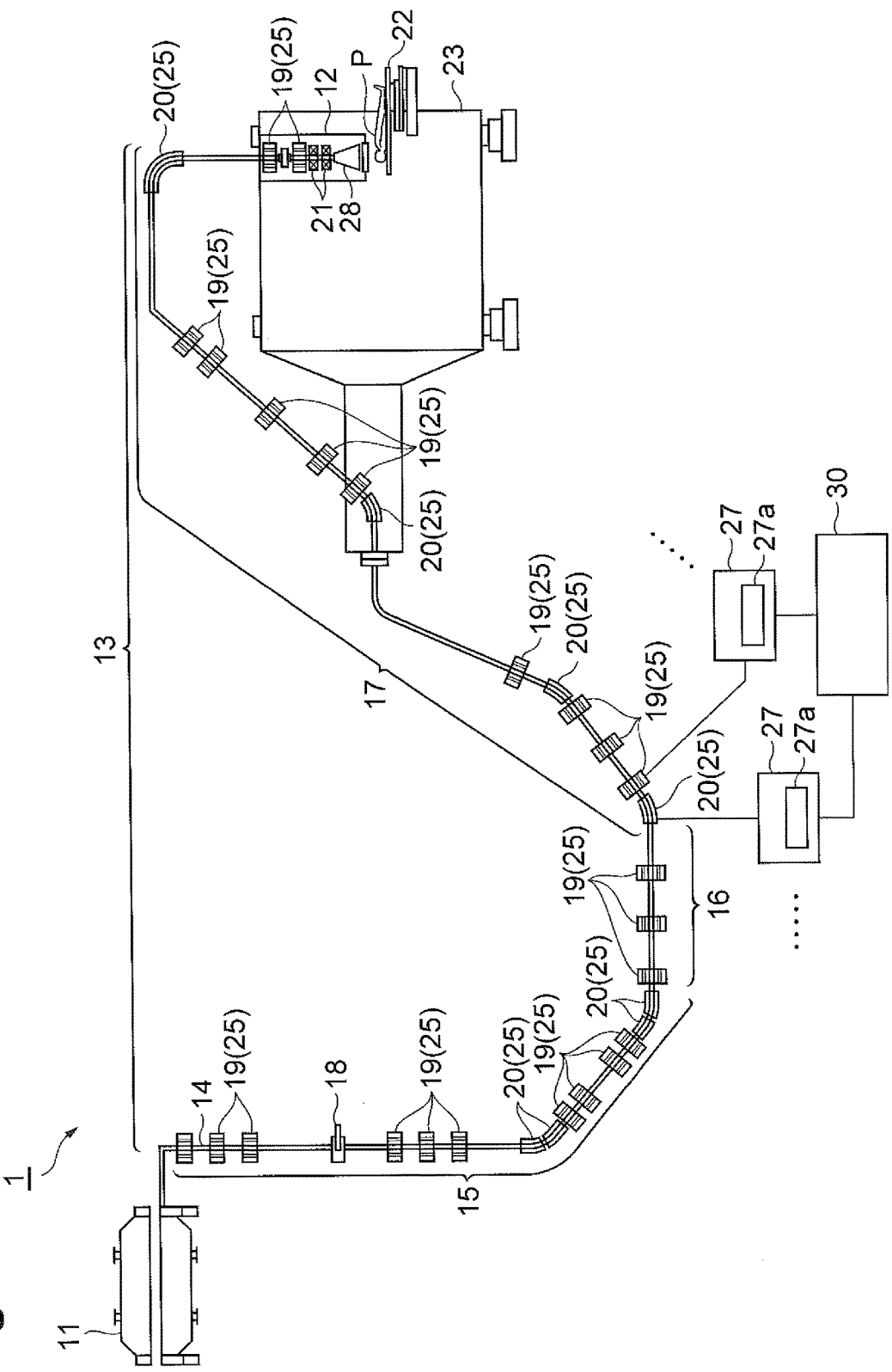
FIG. 1 is a schematic diagram illustrating a charged-particle beam irradiation device according to an embodiment of the invention.

However, as described above, when the charged-particle beam is controlled in synchronization with the breathing of the patient, control becomes complicated. On the other hand, when the irradiation time is not controlled in synchronization with breathing, it is considered that the charged-particle beam is radiated while the patient holds a breath. However, in this case, it takes a lot of time for irradiation with the charged-particle beam and to switch the layer of the irradiated body and it is difficult to complete a treatment while the patient holds a breath. Therefore, the following control process is needed. That is, it is necessary to repeatedly perform the following process: while the patient holds a breath, the charged-particle beam is radiated and the layer is switched; the radiation of the charged-particle beam is interrupted; the patient breathes and the posture of the patient is adjusted; and the charged-particle beam is radiated while the patient holds a breath again. When this control process is performed, the patient needs to hold a breath several times and the burden of the patient increases. Therefore, it is necessary to reduce the burden of the patient while the charged-particle beam therapy apparatus performs treatment.

It is desirable to provide a charged-particle beam therapy apparatus and a method for controlling a charged-particle beam therapy apparatus which can reduce the burden of the patient during treatment.

The inventors conducted a thorough study and found that the irradiation interruption time during one treatment was reduced to shorten the total treatment time. Therefore, in the charged-particle beam therapy apparatus according to the embodiment of the invention, in the control pattern during one treatment which is stored in the control unit, the sum of the irradiation interruption times for which the irradiation of the irradiated body with the charged-particle beam by the irradiation unit is interrupted is set to be shorter than the sum of the irradiation times for which the irradiation unit irradiates the irradiated body with the charged-particle beam. As such, since the sum of the irradiation interruption times is set to be shorter than the sum of the irradiation times during one treatment, it is possible to reduce the total time required for one treatment. As such, when the time required for one treatment is reduced, the charged-particle beam therapy apparatus can complete a treatment while the patient holds a breath and reduce the burden of the patient during treatment.

In the charged-particle beam therapy apparatus according to the embodiment of the invention, the control unit may alternately repeat an irradiation process of radiating the charged-particle beam to one layer set in the irradiated body and a switching process of switching an irradiation target to the next layer. In the control pattern, the irradiation time may be set to each irradiation process, the irradiation interruption time may be set to each switching process, and the irradiation time set to each irradiation process and the irradiation interruption time set to each switching process may be continuously set. As such, in the control pattern, the irradiation time set to the irradiation process and the irradiation interruption time set to the switching process are continuously set. That is, it is not necessary to ensure the time required for the patient to get his or her breath back during each process and the charged-particle beam is radiated to the next layer immediately after the switching of the layer is completed. Therefore, it is possible to reduce the treatment time.

In the charged-particle beam therapy apparatus according to the embodiment of the invention, the irradiation unit may be capable of completing the irradiation of all of the layers set in the irradiated body with the charged-particle beam within 10 seconds. According to this structure, it is possible to complete a treatment while the patient holds a breath and to reduce the burden of the patient during treatment.

The method for controlling a charged-particle beam therapy apparatus according to the embodiment of the invention can have the same operation and effect as the above-mentioned charged-particle beam therapy apparatus.

According to the embodiments of the invention, it is possible to reduce the burden of the patient during treatment.

Hereinafter, embodiments of the invention will be described in detail with reference to the accompanying drawings. In addition, the terms "upstream side" and "downstream side" mean the upstream side (accelerator side) and downstream side (patient side) of an emitted charged-particle beam, respectively.

As illustrated in FIG. 1, a charged-particle beam therapy apparatus 1 is used for cancer treatment using radiation therapy and includes an accelerator 11 that accelerates charged particles and emits a charged-particle beam, an irradiation nozzle 12 (irradiation unit) that irradiates an irradiated body with the charged-particle beam, a beam transport line 13 (transport line) that transports the charged-particle beam emitted from the accelerator 11 to the irradiation nozzle 12, a degrader (energy adjustment unit) 18 that is provided in the beam transport line 13 and reduces the energy of the charged-particle beam in order to adjust the range of the charged-particle beam, a plurality of electromagnets 25 that are provided in the beam transport line 13, electromagnet power supplies 27 that are provided so as to correspond to the plurality of electromagnets 25, and a control unit 30 that controls the overall operation of the charged-particle beam therapy apparatus 1. In this embodiment, a cyclotron is used as the accelerator 11. However, the accelerator 11 is not limited to the cyclotron. For example, the accelerator 11 may be other generation sources that generate the charged-particle beam, such as a synchrotron, a synchrocyclotron, and a linear accelerator.

The charged-particle beam therapy apparatus 1 irradiates a tumor (irradiated body) of a patient P on a treatment table 22 with the charged particle beam emitted from the accelerator 11. The charged-particle beam is obtained by accelerating charged particles at high speed and is, for example, a proton beam or a heavy particle (heavy ion) beam. The charged-particle beam therapy apparatus 1 according to this embodiment irradiates the irradiated body with the charged-particle beam using a so-called scanning method, virtually divides (slices) the irradiated body in a depth direction, and irradiates an irradiation range on a layer in each sliced plane (layer) with the charged-particle beam (for example, see FIGS. 5A to 5C).

In addition, examples of the irradiation method using the scanning method include a spot scanning irradiation method and a raster scanning irradiation method. In the spot scanning irradiation method, when the irradiation of one spot in the irradiation range with the charged-particle beam is completed, the irradiation with the beam (charged-particle beam) is stopped once and the beam is radiated to the next spot after preparation for the irradiation of the next spot with the beam is completed. In contrast, the raster scanning irradiation method continuously irradiates the irradiation range of the same layer with the beam, without interrupting beam irradiation. As such, since the raster scanning irradiation method continuously irradiates the irradiation range on the same layer with the beam, the irradiation range is not formed by a plurality of spots, unlike the spot scanning irradiation method. In the following description, irradiation is performed by the spot scanning irradiation method and the irradiation range on the same layer is formed by a plurality of spots. However, the invention is not limited thereto. For example, when irradiation is performed by the raster scanning irradiation method, as described above, the irradiation range may not be formed by spots.

The irradiation nozzle 12 is provided in the rotating gantry 23 so as to rotate 360 degrees around the treatment table 22 and can be moved to any rotational position by the rotating gantry 23. The irradiation nozzle 12 includes a convergence electromagnet 19 (which will be described in detail below), a scanning electromagnet 21, and a vacuum duct 28. The scanning electromagnet 21 is provided in the irradiation nozzle 12. The scanning electromagnet 21 includes an X-direction scanning electromagnet that performs scanning with the charged-particle beam in the X direction in the plane which intersects the irradiation direction of the charged-particle beam and a Y-direction scanning electromagnet that performs scanning with the charged-particle beam in the Y direction intersecting the X direction in the plane which intersects the irradiation direction of the charged-particle beam. Since the charged-particle beam which is used for scanning by the scanning electromagnet 21 is deflected in the X direction and/or the Y direction, the diameter of the vacuum duct 28 which is provided on the downstream side of the scanning electromagnet increases toward the downstream side.

The beam transport line 13 includes a vacuum duct 14 through which the charged-particle beam passes. The inside of the vacuum duct 14 is maintained in a vacuum state such that the charged particles forming the charged-particle beam are prevented from being scattered due to, for example, air during transport.

The beam transport line 13 includes an energy selection system (ESS) 15 that selectively extracts a charged-particle beam with an energy width narrower than a predetermined energy width from the charged-particle beams with the predetermined energy width which are emitted from the accelerator 11, a beam transport system (BTS) 16 that transports the charged-particle beam with the energy width selected by the ESS 15 while maintaining the energy of the charged-particle beam, and a gantry transport system (GTS) 17 that transports the charged-particle beam from the BTS 16 to the rotating gantry 23.

The degrader 18 reduces the energy of the passing charged-particle beam in order to adjust the range of the charged-particle beam. The depth from the surface of the body of the patient to the tumor, which is the irradiated body, varies depending on the patient. Therefore, when the patient is irradiated with the charged-particle beam, it is necessary to adjust the range which is the penetration depth of the charged-particle beam. The degrader 18 adjusts the energy of the charged-particle beam which is emitted with a constant energy level from the accelerator 11 such that the charged-particle beam appropriately reaches the irradiated body that is disposed at a predetermined depth in the body of the patient. The adjustment of the energy of the charged-particle beam by the degrader 18 is performed for each of the layers obtained by slicing the irradiated body.

A plurality of electromagnets 25 are provided in the beam transport line 13 and are used to adjust the charged-particle beam such that the beam transport line 13 can transport the charged-particle beam using a magnetic field. As the electromagnets 25, the following electromagnets are used: a convergence electromagnet 19 that converges the diameter of the charged-particle beam which is being transported; and a deflection electromagnet 20 that deflects the charged-particle beam. In the following description, in some cases, the convergence electromagnet 19 and the deflection electromagnet 20 are referred to as the electromagnet 25, without being distinguished from each other. A plurality of electromagnets 25 are provided on at least the downstream side of the degrader 18 in the beam transport line 13. However, in this embodiment, the electromagnets 25 are also provided on the upstream side of the degrader 18. The convergence electromagnet 19 is also provided as the electromagnet 25 on the upstream side of the degrader 18 in order to converge the diameter of the charged-particle beam before the degrader 18 adjusts the energy. The total number of electromagnets 25 can be flexibly changed according to, for example, the length of the beam transport line 13 and is, for example, about 10 to 40. In FIG. 1, only some of the electromagnet power supplies 27 are illustrated. However, in practice, the number of electromagnet power supplies 27 is equal to the number of electromagnets 25.

The position of the degrader 18 and the electromagnet 25 in the beam transport line 13 is not particularly limited. However, in this embodiment, the degrader 18, the convergence electromagnet 19, and the deflection electromagnet 20 are provided in the ESS 15. The convergence electromagnet 19 is provided in the BTS 16 and the convergence electromagnet 19 and the deflection electromagnet 20 are provided in the GTS 17. As described above, the degrader 18 is provided in the ESS 15 between the accelerator 11 and the rotating gantry 23. Specifically, the degrader 18 is provided (on the upstream side) closer to the accelerator 11 than to the rotating gantry 23 in the ESS 15.

The electromagnet power supply 27 supplies a current to the corresponding electromagnet 25 such that the electromagnet 25 generates a magnetic field. The electromagnet power supply 27 can adjust the current supplied to the corresponding electromagnet 25 in order to set the intensity of the magnetic field of the corresponding electromagnet 25. The electromagnet power supply 27 adjusts the current supplied to the electromagnet 25 on the basis of a signal from the control unit 30 (which will be described in detail below). The electromagnet power supplies 27 are provided in one-to-one correspondence with the electromagnets 25. That is, the number of electromagnet power supplies 27 is equal to the number of electromagnets 25.

The relationship between the depth of each layer of the irradiated body and the current supplied to the electromagnet 25 is as follows. That is, the energy of the charged-particle beam which is required to irradiate each layer with the charged-particle beam is determined from the depth of each layer and the amount of energy adjusted by the degrader 18 is determined from the depth of each layer. When the energy of the charged-particle beam is changed, the intensity of the magnetic field required to deflect and converge the charged-particle beam is also changed. Therefore, the current supplied to the electromagnet 25 is determined such that the intensity of the magnetic field of the electromagnet 25 corresponds to the amount of energy adjusted by the degrader 18.

Figure 2:
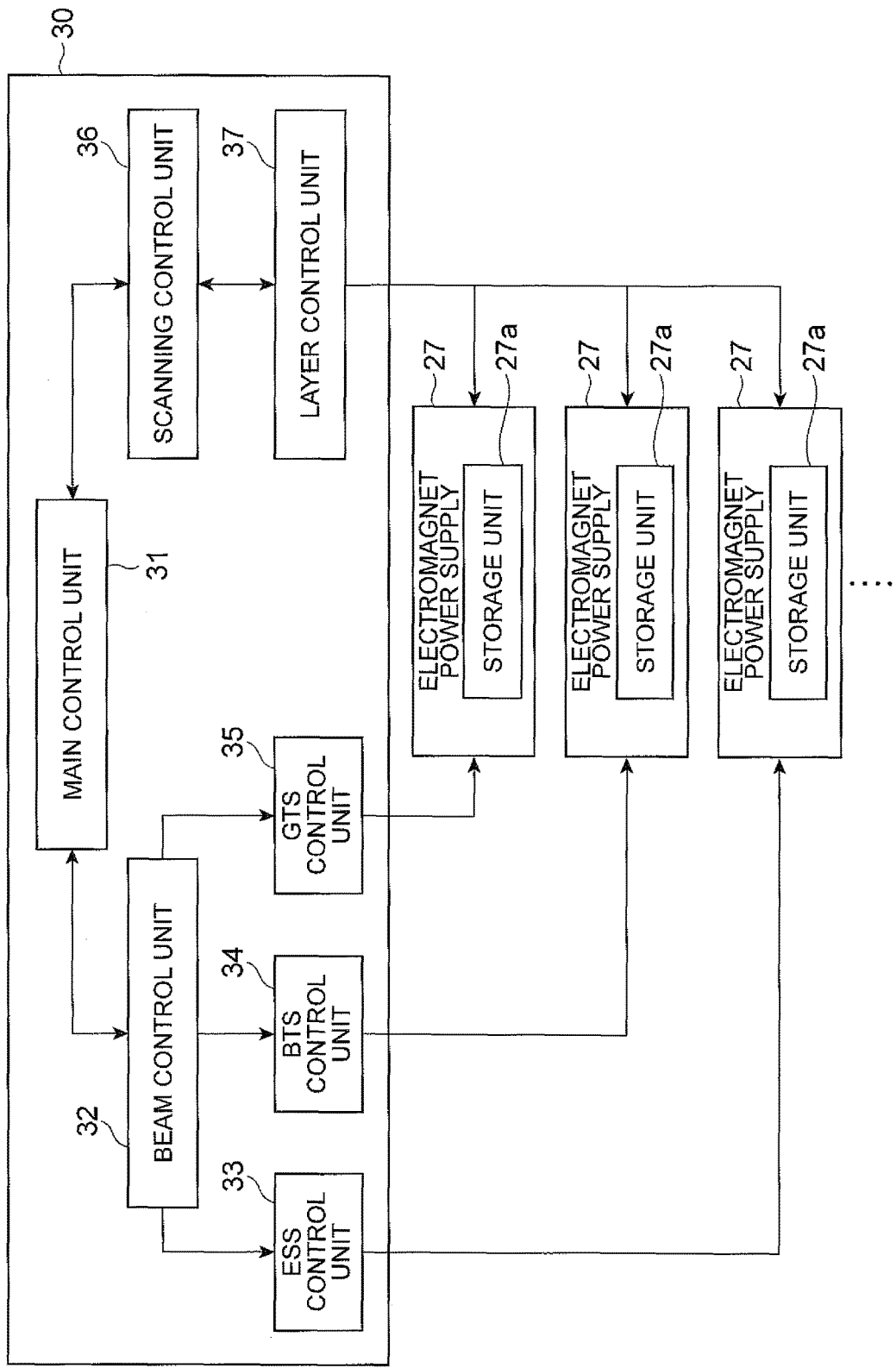
FIG. 2 is a block diagram illustrating the functions of a control unit.

Next, the control unit 30 and the electromagnet power supply 27 will be described in detail with reference to FIG. 2. In FIG. 2, only three electromagnet power supplies 27 are illustrated. However, in practice, the number of electromagnet power supplies 27 is equal to the number of electromagnets 25 provided in the charged-particle beam therapy apparatus 1. In addition, in FIG. 2, the electromagnet 25 is not illustrated. However, in practice, the electromagnet 25 which is electrically connected to the electromagnet power supply 27 is provided.

The control unit 30 controls the irradiation of the irradiated body with the charged-particle beam from the accelerator 11. The control unit 30 includes a main control unit 31, a beam control unit 32, an ESS control unit 33, a BTS control unit 34, a GTS control unit 35, a scanning control unit 36, and a layer control unit 37.

The main control unit 31 controls the beam control unit 32 and the scanning control unit 36. Specifically, the main control unit 31 transmits a process start signal to the beam control unit 32 and the scanning control unit 36 to start a process and transmits a process end signal to the beam control unit 32 and the scanning control unit 36 to end the process.

The beam control unit 32 controls each function such that the charged-particle beam can be radiated to the irradiated body. Specifically, the beam control unit 32 transmits a process start signal to a cyclotron control unit (not illustrated) in response to the process start signal from the main control unit 31 such that the accelerator 11 emits the charged-particle beam. The beam control unit 32 transmits a process start signal to the ESS control unit 33, the BTS control unit 34, and the GTS control unit 35 in response to the process start signal from the main control unit 31.

The ESS control unit 33 turns on the electromagnet power supplies 27 corresponding to the electromagnets 25 provided in the ESS 15 in response to the process start signal from the beam control unit 32. Similarly, the BTS control unit 34 turns on the electromagnet power supplies 27 corresponding to the electromagnets 25 provided in the BTS 16 in response to the process start signal from the beam control unit 32. Similarly, the GTS control unit 35 turns on the electromagnet power supplies 27 corresponding to the electromagnets 25 provided in the GTS 17 in response to the process start signal from the beam control unit 32. The charged-particle beam emitted from the accelerator 11 can be radiated to the irradiated body by the control of the accelerator 11 by the beam control unit 32 and the control of the electromagnet power supplies 27 by the ESS control unit 33, the BTS control unit 34, and the GTS control unit 35. Thereafter, the control process of the scanning control unit 36 is performed.

The scanning control unit 36 controls the scanning of the irradiated body with the charged-particle beam. The scanning control unit 36 transmits an irradiation start signal to the scanning electromagnet 21 in response to the process start signal from the main control unit 31 such that the charged-particle beam is radiated to a plurality of irradiation spots on the same layer by the scanning electromagnet 21. Information about the irradiation spots on each layer is stored in the scanning control unit 36 in advance. When the irradiation of all of the spots on one layer with the charged-particle beam by the scanning electromagnet 21 is completed, the scanning control unit 36 transmits a layer switching signal to the layer control unit 37. The layer switching signal includes information for specifying the switched layer (for example, a second layer).

Figure 5A:
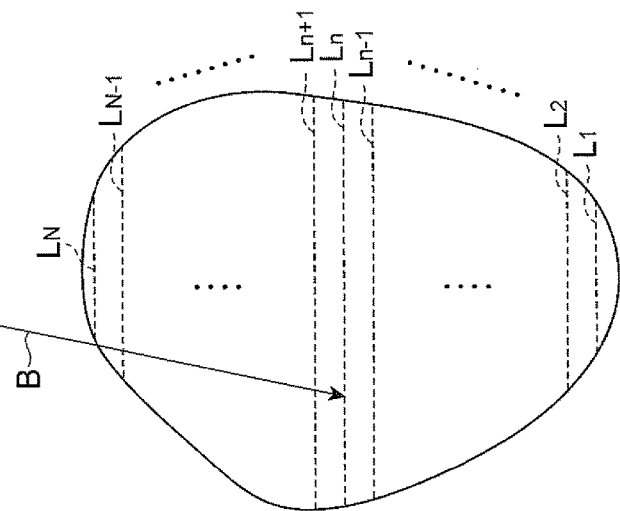
FIGS. 5A to 5C are diagrams illustrating the setting of parameters and an irradiation image of a charged-particle beam.
Figure 5B:
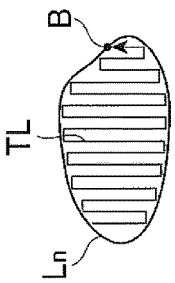
Figure 5C:
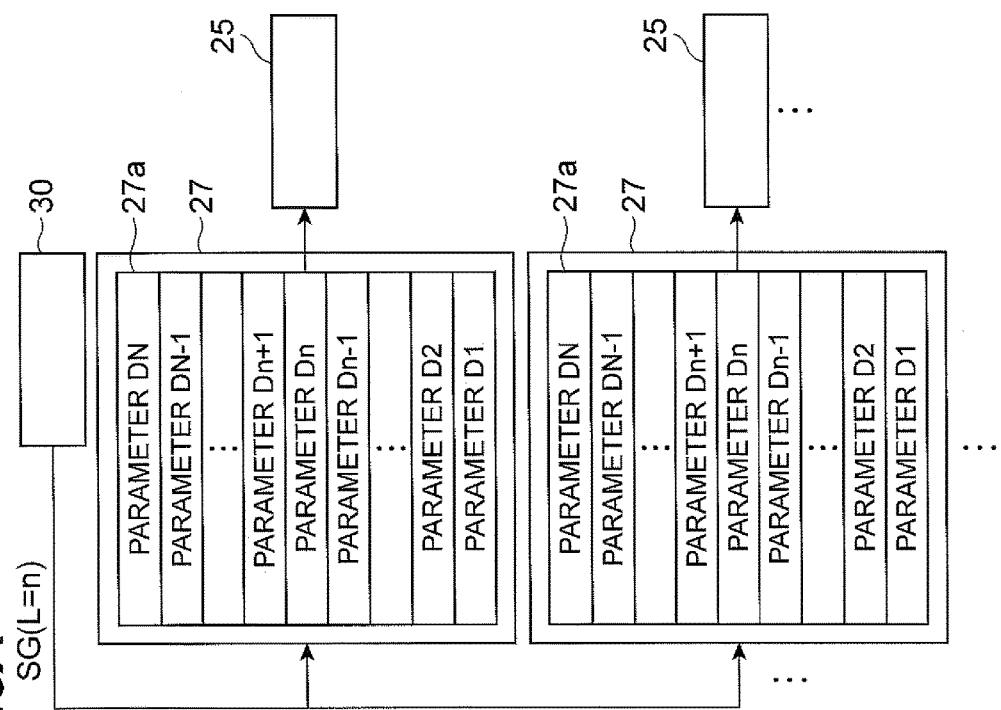

The charged-particle beam irradiation image of the scanning electromagnet 21 corresponding to the control of the scanning control unit 36 will be described with reference to FIGS. 5B and 5C. FIG. 5B illustrates the irradiated body which is virtually sliced into a plurality of layers in the depth direction. FIG. 5C illustrates the scanning image of the charged-particle beam in one layer as seen from the irradiation direction of the charged-particle beam.

As illustrated in FIG. 5B, the irradiated body is virtually sliced into a plurality of layers in the depth direction. In this example, the irradiated body is virtually sliced into N layers, that is, a layer $L_1$, a layer $L_2$, ..., a layer $L_{n-1}$, a layer $L_n$, a layer $L_{n+1}$, ..., a layer $L_{N-1}$, and a layer $L_N$ in order of the depth (the range of an irradiation beam B which is a charged-particle beam). As illustrated in FIG. 5C, the irradiation beam B is radiated to a plurality of irradiation spots on the layer $L_n$ while drawing a beam trajectory TL. That is, the irradiation nozzle 12 controlled by the scanning control unit 36 is moved along the beam trajectory TL.

Returning to FIG. 2, the layer control unit 37 performs a process related to the switching of the layer in response to the layer switching signal from the scanning control unit 36. The process related to the switching of the layer includes a degrader setting process of changing the amount of energy adjusted by the degrader 18 and an electromagnet setting process of setting the parameter of the electromagnet 25 so as to correspond to the amount of energy adjusted by the degrader 18 after the degrader setting process. The parameter of the electromagnet 25 is the target value of the current supplied to the electromagnet 25.

In the charged-particle beam therapy, when a given patient is treated, plans for how to irradiate the patient with the charged-particle beam are made (treatment planning). Treatment planning data which is determined during the treatment planning is transmitted from a treatment planning device (not illustrated) to the layer control unit 37 of the control unit 30 before a treatment is performed and is then stored in the layer control unit 37. The treatment planning data includes, for example, the amount of energy adjusted by the degrader 18, which is used to irradiate each layer of the irradiated body with the charged-particle beam, and the parameter of the electromagnet 25 for radiating the charged-particle beam to all layers which corresponds to the amount of energy adjusted by the degrader 18.

First, the layer control unit 37 performs a degrader setting process as the process related to the switching of the layer. As described above, the layer control unit 37 stores the amount of energy adjusted by the degrader 18, which is used to irradiate each layer of the irradiated body with the charged-particle beam, in advance. Then, the layer control unit 37 sets the amount of energy adjusted by the degrader 18 to a value corresponding to the switched layer, in response to the layer switching signal from the scanning control unit 36.

The layer control unit 37 performs the electromagnet setting process after the degrader setting process. Specifically, the layer control unit 37 transmits the layer switching signal to the electromagnet power supplies 27 at the same time such that the parameter of the electromagnet 25 corresponds to the amount of energy adjusted by the degrader 18 after the degrader setting process. The layer switching signal transmitted from the layer control unit 37 to the electromagnet power supply 27 simply includes information for specifying the switched layer and does not include the parameter of the electromagnet 25 corresponding to the switched layer (the parameter of the electromagnet 25 corresponding to the amount of energy adjusted by the degrader 18 after the degrader setting process). The electromagnet power supply 27 changes the parameter of the electromagnet 25. On the premise of the parameter change process, the layer control unit 37 transmits, to the electromagnet power supply 27, the parameter of the electromagnet 25, which corresponds to the amount of energy adjusted by the degrader 18 and is used to irradiate all layers with the beam, in the treatment planning data before irradiation starts (not immediately before the beam is radiated to the layer (the layer is switched), but before a treatment starts).

The electromagnet power supply 27 sets the parameter of the electromagnet 25 corresponding to the switched layer (the parameter of the electromagnet 25 corresponding to the amount of energy adjusted by the degrader 18 after the degrader setting process) on the basis of the layer switching signal received from the layer control unit 37. Specifically, the electromagnet power supply 27 includes a storage unit 27a that stores the parameter of the electromagnet 25 corresponding to each layer. When receiving the layer switching signal from the layer control unit 37, the electromagnet power supply 27 sets a parameter corresponding to the switched layer which is included in the layer switching signal. In this way, a current corresponding to the switched layer is supplied to the electromagnet 25.

The setting of the parameter by the electromagnet power supply 27 will be described with reference to FIG. 5A. As illustrated in FIG. 5A, each electromagnet power supply 27 stores the parameters $D_1$ to $D_N$ of the electromagnets 25 corresponding to each layer of the irradiated body, specifically, the layers $L_1$ to $L_N$ (see FIG. 5B). Then, the electromagnet power supply 27 sets the parameter $D_n$ on the basis of information (L=n) for specifying the switched layer which is included in a layer switching signal SG transmitted from the layer control unit 37.

When it is determined that the setting of the parameter by the electromagnet power supply 27 has been completed after a predetermined period of time (for example, 50 msec to 200 msec) has elapsed from the transmission of the layer switching signal to the electromagnet power supply 27, the layer control unit 37 transmits a switching completion signal to the scanning control unit 36. Then, the scanning control unit 36 transmits an irradiation start signal to the scanning electromagnet 21 in response to the switching completion signal.

Figure 3:
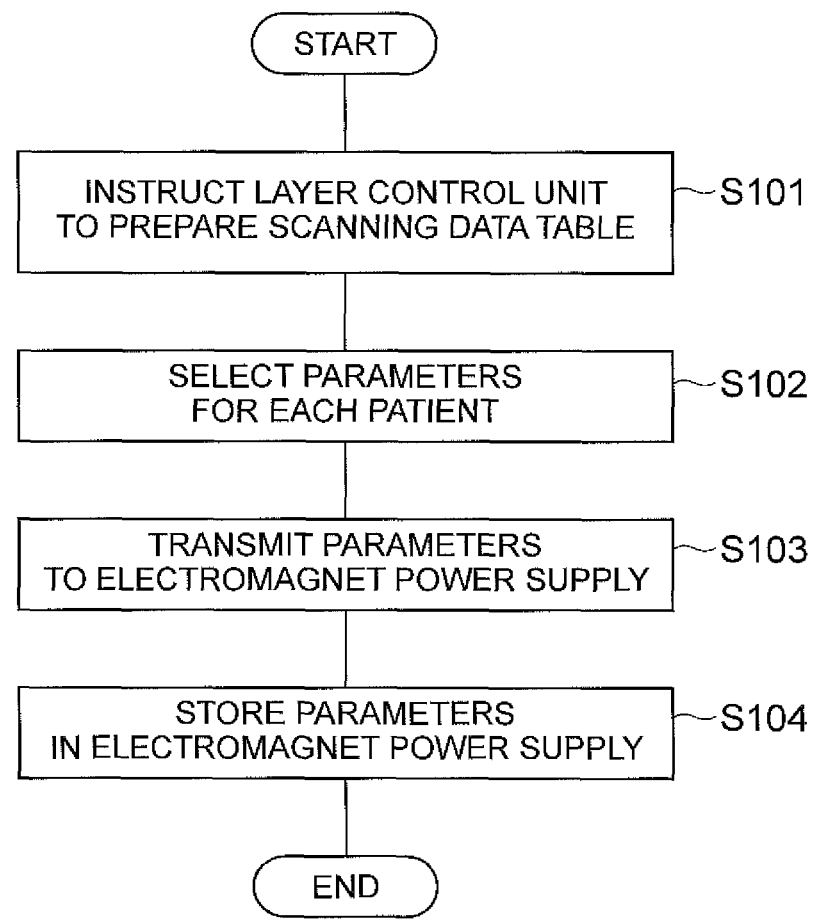
FIG. 3 is a flowchart illustrating the content of a process in a parameter preparation stage.

Next, a process of preparing (storing) the parameter of the electromagnet 25 in the storage unit 27a of the electromagnet power supply 27 will be described with reference to FIG. 3.

First, the layer control unit 37 reads a scanning data table from the treatment planning device (S101). The energy of the charged-particle beam corresponding to the irradiated body is considered as the parameter of the electromagnet 25 for each layer and is set in advance.

Then, the layer control unit 37 selects the parameter of the electromagnet 25 as information to be transmitted to the electromagnet power supply 27 (S102). The parameter of the electromagnet 25 is managed for each layer.

Then, the layer control unit 37 transmits the parameter of the electromagnet 25 to the electromagnet power supply 27 (S103). For example, the parameters of the electromagnets 25 for all layers are lumped together and are sequentially transmitted to each electromagnet power supply 27.

Finally, the parameters of the electromagnets 25 for all layers which are transmitted from the layer control unit 37 are stored in the storage units 27a of the electromagnet power supplies 27. The process of storing the parameter of the electromagnet 25 in the storage unit 27a has been described above. When the storage process is completed, a process of setting the parameter of the electromagnet 25 can be performed by cooperation between the layer control unit 37 and the electromagnet power supply 27 during the switching of the layer.

Next, the parameter setting process during the switching of the layer will be described with reference to FIG. 4 and FIGS. 5A to 5C. On the premise of the process, the parameter of the electromagnet 25 needs to be prepared (stored) in the storage unit 27a of the electromagnet power supply 27 and the charged-particle beam needs to be radiated from the accelerator 11 to the irradiated body by the control of the accelerator 11 by the beam control unit 32 and the control of the electromagnet power supplies 27 by the ESS control unit 33, the BTS control unit 34, and the GTS control unit 35.

An example in which the charged-particle beam is radiated to the layers $L_1$ to $L_N$ of the irradiated body illustrated in FIG. 5B will be described. On the premise of the following process, settings for radiating the charged-particle beam to the layer $L_1$, which is the deepest layer of the irradiated body, are performed. Specifically, the electromagnet power supply 27 sets the parameter $D_1$ of the electromagnet 25 corresponding to the layer $L_1$.

First, the charged-particle beam is radiated to all irradiation spots on the layer $L_1$ of the irradiated body by the scanning electromagnet 21 on the basis of the irradiation start signal from the scanning control unit 36 (S201). When the irradiation of all irradiation spots on the layer $L_1$ with the charged-particle beam is completed, the scanning control unit 36 transmits the layer switching signal SG to the layer control unit 37 (S202). The layer switching signal SG includes information (L=2) for specifying the switched layer $L_2$.

Then, the layer control unit 37 changes the amount of energy adjusted by the degrader 18 on the basis of the layer switching signal SG from the scanning control unit 36 (S203). Specifically, the layer control unit 37 changes the amount of energy adjusted by the degrader 18 to a value corresponding to the switched layer $L_2$, on the basis of the information (L=2) which is included in the layer switching signal SG and is used to specify the switched layer $L_2$ and information about the amount of energy adjusted by the degrader 18 which is stored in advance and is used to irradiate each layer of the irradiated body with the charged-particle beam.

Then, the layer control unit 37 transmits the layer switching signal SG to each electromagnet power supply 27 (S204). The layer switching signal SG transmitted from the layer control unit 37 to each electromagnet power supply 27 simply includes the information (L=2) for specifying the switched layer $L_2$ and does not include the parameter $D_2$ of the electromagnet 25 corresponding to the switched layer $L_2$ (the parameter $D_2$ of the electromagnet 25 corresponding to the amount of energy adjusted by the degrader 18 after the degrader setting process).

Then, the electromagnet power supply 27 sets the parameter $D_2$ of the electromagnet 25 corresponding to the switched layer $L_2$ (the parameter $D_2$ of the electromagnet 25 corresponding to the amount of energy adjusted by the degrader 18 after the degrader setting process) on the basis of the layer switching signal SG received from the layer control unit 37 (S205). In this way, a current corresponding to the switched layer $L_2$ is supplied to the electromagnet 25 and the charged-particle beam can be appropriately radiated to the switched layer $L_2$.

Finally, the layer control unit 37 transmits a switching completion signal to the scanning control unit 36 (S206). The parameter setting process when the layer is switched has been described above. When receiving the switching completion signal transmitted from the layer control unit 37, the scanning control unit 36 transmits the irradiation start signal to the scanning electromagnet 21. The process from S201 to S206 is repeatedly performed in order to set parameters during the switching of each layer. That is, for example, when the layer is switched from the layer $L_{n-1}$ to the layer $L_n$, the process from S201 to S206 is also performed in order to set the parameter of the switched layer $L_n$. Finally, when the process of S201 (the irradiation of all spots with the charged-particle beam) for the layer $L_N$ is completed, the scanning control unit 36 transmits, to the main control unit 31, an irradiation completion signal indicating that the irradiation of all of the layers of the irradiated body with the charged-particle beam has been completed, and the radiation treatment for the patient is completed.

Next, the operation and effect of this embodiment will be described. In the charged-particle beam therapy apparatus 1 according to this embodiment, when the layer of the irradiated body to which the charged-particle beam is radiated is switched, the layer control unit 37 transmits the layer switching signal including information for specifying the switched layer to the electromagnet power supply 27.

In the charged-particle beam therapy apparatus, when the layer of the irradiated body is switched, it is necessary to change the energy of the charged-particle beam to a value corresponding to the switched layer and to change the parameter of the electromagnet (for example, the current supplied to the electromagnet) in order to appropriately irradiate the switched layer with the charged-particle beam whose energy has been changed. In the related art, when the layer of the irradiated body is switched, the device for controlling the electromagnet power supply transmits the parameter related to the switched layer of the corresponding electromagnet to each electromagnet power supply each time. The electromagnets have different parameters and the parameters include a plurality of information items, such as the current supplied to the electromagnet. It takes a lot of time for data communication between the device for controlling the electromagnet power supplies and each electromagnet power supply (for example, about 1 second). Therefore, it takes a lot of time to switch the layer.

Therefore, in the charged-particle beam therapy apparatus 1 according to this embodiment, the electromagnet power supply 27 includes the storage unit 27a that stores the parameter of the electromagnet 25 for each layer of the irradiated body. As described above, when the layer is switched, the layer control unit 37 transmits the layer switching signal including the information for specifying the switched layer to the electromagnet power supply 27. Therefore, the electromagnet power supply 27 can set the parameter of the electromagnet 25 for the switched layer, which is stored in the storage unit 27a, on the basis of the layer switching signal transmitted from the layer control unit 37. As such, since the storage unit 27a of the electromagnet power supply 27 stores the parameter of the electromagnet 25 for each layer, the device (layer control unit 37) for controlling the electromagnet power supply does not need to transmit the parameter of each layer to the electromagnet power supply 27 during the switching of the layer and may simply transmit a signal indicating the switching time (a layer switching signal including information for specifying the switched layer). In this case, it is possible to significantly reduce the time required for data communication between the layer control unit 37 and each electromagnet power supply 27 (for example, 10 msec). Therefore, it is possible to reduce the switching time of the layer and thus to reduce the irradiation time.

As described above, the layer switching signal transmitted from the layer control unit 37 to the electromagnet power supply 27 includes the information for specifying the layer. The electromagnet power supply 27 sets the parameter of the electromagnet 25 corresponding to the specified layer, on the basis of the information for specifying the layer, which is included in the layer switching signal, and the parameter of the electromagnet 25 corresponding to each layer, which is stored in the storage unit 27a. As such, since the information for specifying the layer is included in the layer switching signal, the electromagnet power supply 27 can uniquely specify the parameter of the layer to be set after switching. As a result, it is easy to switch the layer.

Since the irradiation nozzle 12 is attached to the rotating gantry 23 which can be rotated around the irradiated body, it is possible irradiate the irradiated body with the charged-particle beam in the multiple directions. Therefore, it is possible to effectively irradiate the irradiated body with the charged-particle beam.

Since the degrader 18 is provided between the accelerator 11 and the rotating gantry 23, it is possible to reliably adjust the energy of the charged-particle beam emitted from the accelerator 11 before the charged-particle beam is radiated to the irradiated body.

Here, the degrader 18 receives the charged-particle beam and reduces the energy of the charged-particle beam. In addition, the degrader 18 is highly activated and emits gamma rays or neutron rays. When the degrader 18 is arranged close to the rotating gantry 23 (that is, the irradiated body), there is a concern that a radiation dose in a structure related to irradiation in the irradiated body will increase. For this reason, the degrader 18 is provided closer to the accelerator 11 than to the rotating gantry 23 and adjusts energy at the position that is sufficiently far away from the irradiated body. Therefore, it is possible to prevent a radiation dose from increasing in the structure related to irradiation in the irradiated body.

The structure of the charged-particle beam therapy apparatus is not limited to the above-described embodiment and may be modified without departing from the scope of the claims or may be applied to other structures.

For example, in the above-described embodiment, the scanning control unit 36 and the layer control unit 37 are individually provided. However, the scanning control unit 36 and the layer control unit 37 may be integrated into one unit having the functions of the scanning control unit 36 and the layer control unit 37. Similarly, in the above-described embodiment, the beam control unit 32 and the scanning control unit 36 are individually provided. However, the beam control unit 32 and the scanning control unit 36 may be integrated into one unit having the functions of the beam control unit 32 and the scanning control unit 36. In addition, in the above-described embodiment, the layer switching signal transmitted from the layer control unit 37 to the electromagnet power supply 27 includes the information for specifying the layer. However, the layer switching signal does not necessarily include the information for specifying the layer and may simply include a signal indicating the switching time of the layer. In this case, the storage unit of the electromagnet power supply needs to store the irradiation order of each layer and the parameter set by the electromagnet power supply needs to be constantly managed. In this case, even though the layer switching signal is simply the signal indicating the switching time of the layer, it is possible to specify and set the parameter of the electromagnet corresponding to the switched layer.

The irradiation nozzle may be fixed, without using the rotating gantry 23, and fixed irradiation may be performed. Furthermore, in addition to the degrader 18, another degrader may be provided closer to the rotating gantry than to the cyclotron.

Next, a method for controlling the charged-particle beam therapy apparatus 1 according to this embodiment will be described. The control unit 30 of the charged-particle beam therapy apparatus 1 stores the control pattern of the apparatus during one treatment. The term "one treatment" means radiating the charged-particle beam to all of the layers $L_1$ to $L_N$ of the irradiated body. The one treatment is from the start of the scanning for the layer $L_1$ to the end of scanning for the last layer $L_N$. The control pattern is information included in the treatment planning data which is created by the treatment planning device (not illustrated). Therefore, the control unit 30 receives the treatment planning data transmitted from the treatment planning device and stores the treatment control pattern of the charged-particle beam therapy apparatus.

Figure 6A:
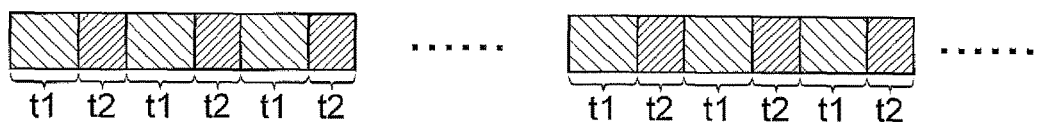
FIG. 6A is a conceptual diagram illustrating the control pattern of a charged-particle beam irradiation device according to the embodiment.

FIG. 6A is a conceptual diagram illustrating the control pattern of the charged-particle beam therapy apparatus 1 according to the embodiment. The control unit 30 alternately repeats an irradiation process of radiating the charged-particle beam to one layer $L_n$ set in the irradiated body and a switching process of switching the irradiation target to the next layer $L_{n+1}$. In the control pattern, an irradiation time t1 is set to each irradiation process and an irradiation interruption time t2 is set to each switching process. In the control pattern, the irradiation time t1 for each irradiation process and the irradiation interruption time t2 for each switching process are continuously set. The continuous setting of the irradiation time t1 and the irradiation interruption time t2 means that no process is interposed between one irradiation process and one switching process. That is, immediately after one irradiation process is completed in the irradiation time t1, the switching process starts. Immediately after the one switching process is completed in the irradiation interruption time t2, the next irradiation process starts.

Figure 7:
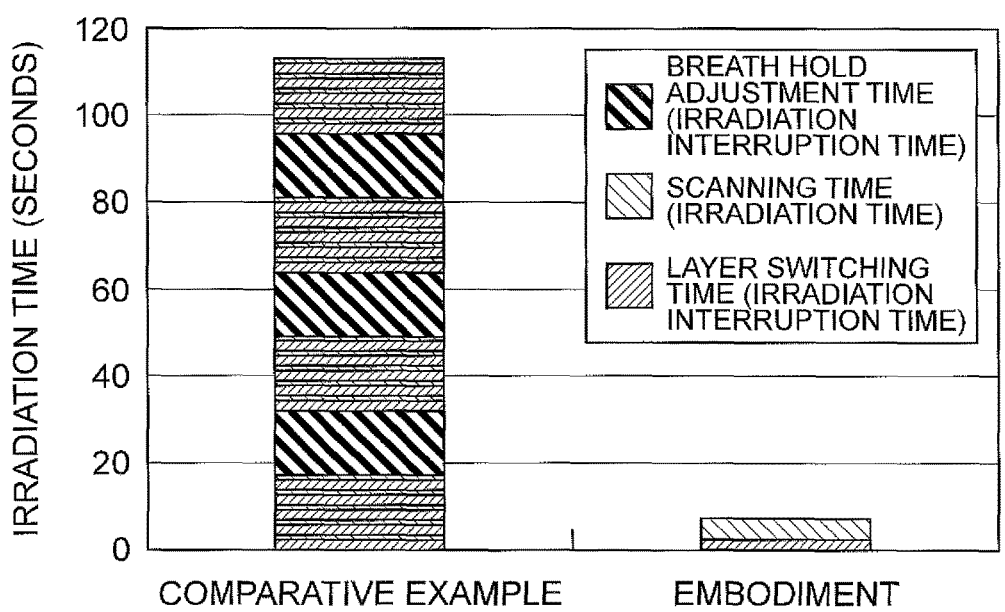
FIG. 7 is a graph illustrating the relationship between an irradiation time and an irradiation interruption time according to the embodiment and the comparative example

In the control pattern, the irradiation interruption time t2 for one switching process is set to be shorter than the irradiation time t1 for one irradiation process. For example, the irradiation interruption time t2 is set to about 100 milliseconds. In the control pattern according to this embodiment, the irradiation process and the switching process are alternately repeated. However, the control pattern does not include a patient's breath hold adjustment process. Therefore, in the entire control pattern, the irradiation interruption time is formed only by the time of the switching process (irradiation interruption time t2). Therefore, as illustrated in FIG. 7, the sum of the irradiation interruption times during one treatment is set to be shorter than the sum of the irradiation times during one treatment. As illustrated in FIG. 7, the irradiation nozzle 12 can complete the irradiation of all of the layers set in the irradiated body with the charged-particle beam within 10 seconds. That is, since one treatment is completed within 10 seconds, it is possible to complete a treatment while the patient holds a breath. When a treatment is performed using the charged-particle beam therapy apparatus 1 according to this embodiment, it is possible to omit the patient's breath hold adjustment process. In the graph illustrated in FIG. 7, a "scanning time" indicates the sum of the irradiation times t1 and a "layer switching time" indicates the sum of the irradiation interruption times t2.

Figure 6B:
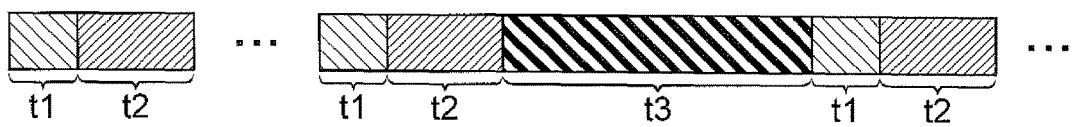
FIG. 6B is a conceptual diagram illustrating the control pattern of a charged-particle beam irradiation device according to a comparative example.

Here, as a comparative example, the control pattern of the charged-particle beam therapy apparatus according to the related art will be described with reference to FIG. 6B. In the control pattern of the charged-particle beam therapy apparatus according to the comparative example, the irradiation interruption time t2 for one switching process is set to be longer than the irradiation time t1 for one irradiation process. For example, the irradiation interruption time t2 is set to about 2 seconds. In addition, in the control pattern according to the comparative example, the irradiation process and the switching process are alternately repeated a predetermined number of times and the breath hold adjustment process is interposed after a predetermined period of time has elapsed. In the breath hold adjustment process, when the patient who holds a breath breathes, for example, a posture for holding a breath again is adjusted. An irradiation interruption time t3 is set to the breath hold adjustment process. In the entire control pattern, the irradiation interruption time is formed by the time of the switching process (irradiation interruption time t2) and a breath hold adjustment time (irradiation interruption time t3). Therefore, as illustrated in FIG. 7, the sum of the irradiation interruption times during one treatment is set to be longer than the sum of the irradiation times during one treatment. In the charged-particle beam therapy apparatus according to the comparative example, since the time required for the switching process is particularly long, it is difficult to complete the irradiation of all layers with the charged-particle beam while the patient holds a breath. Therefore, it is necessary to ensure the breath hold adjustment time during a treatment and the treatment time increases. As illustrated in FIG. 7, it is necessary to perform the breath hold adjustment process a plurality of times and 110 seconds or more are required for one treatment. The graph according to the comparative example illustrated in FIG. 7 is a conceptual diagram.

As described above, in the charged-particle beam therapy apparatus 1 according to this embodiment, in the control pattern for one treatment which is stored in the control unit 30, the sum of the irradiation interruption times for which the radiation of the charged-particle beam by the irradiation nozzle 12 is interrupted (here, the sum of the irradiation interruption times t2 for the switching process) is set to be shorter than the sum of the irradiation times for which the charged-particle beam is radiated by the irradiation nozzle 12 (the sum of the irradiation times t1). As such, since the sum of the irradiation interruption times during one treatment is set to be shorter than the sum of the irradiation times, it is possible to reduce the total time required for one treatment. Therefore, the charged-particle beam therapy apparatus 1 can complete a treatment while the patient holds a breath hold. As a result, it is possible to reduce the burden of the patient during treatment.

In the charged-particle beam therapy apparatus 1 according to this embodiment, the control unit 30 alternately repeats the irradiation process of radiating the charged-particle beam to one layer set in the irradiated body and the switching process of switching the irradiation target to the next layer. In the control pattern, the irradiation time t1 is set to each irradiation process, the irradiation interruption time t2 is set to each switching process, and the irradiation time t1 for each irradiation process and the irradiation interruption time t2 for each switching process are continuously set. As such, in the control pattern, the irradiation time t1 for the irradiation process and the irradiation interruption time t2 for the switching process are alternately and continuously set. That is, the time for which the patient gets his or her breath back does not need to be ensured during each process and the charged-particle beam is radiated to the next layer immediately after the switching of the layer is completed. Therefore, it is possible to reduce the treatment time.

In the charged-particle beam therapy apparatus 1 according to the embodiment of the invention, the irradiation nozzle 12 can complete the irradiation of all of the layers set in the irradiated body with the charged-particle beam within 10 seconds. Therefore, it is possible to complete a treatment while the patient holds a breath and to reduce the burden of the patient during treatment.

Figure 8:
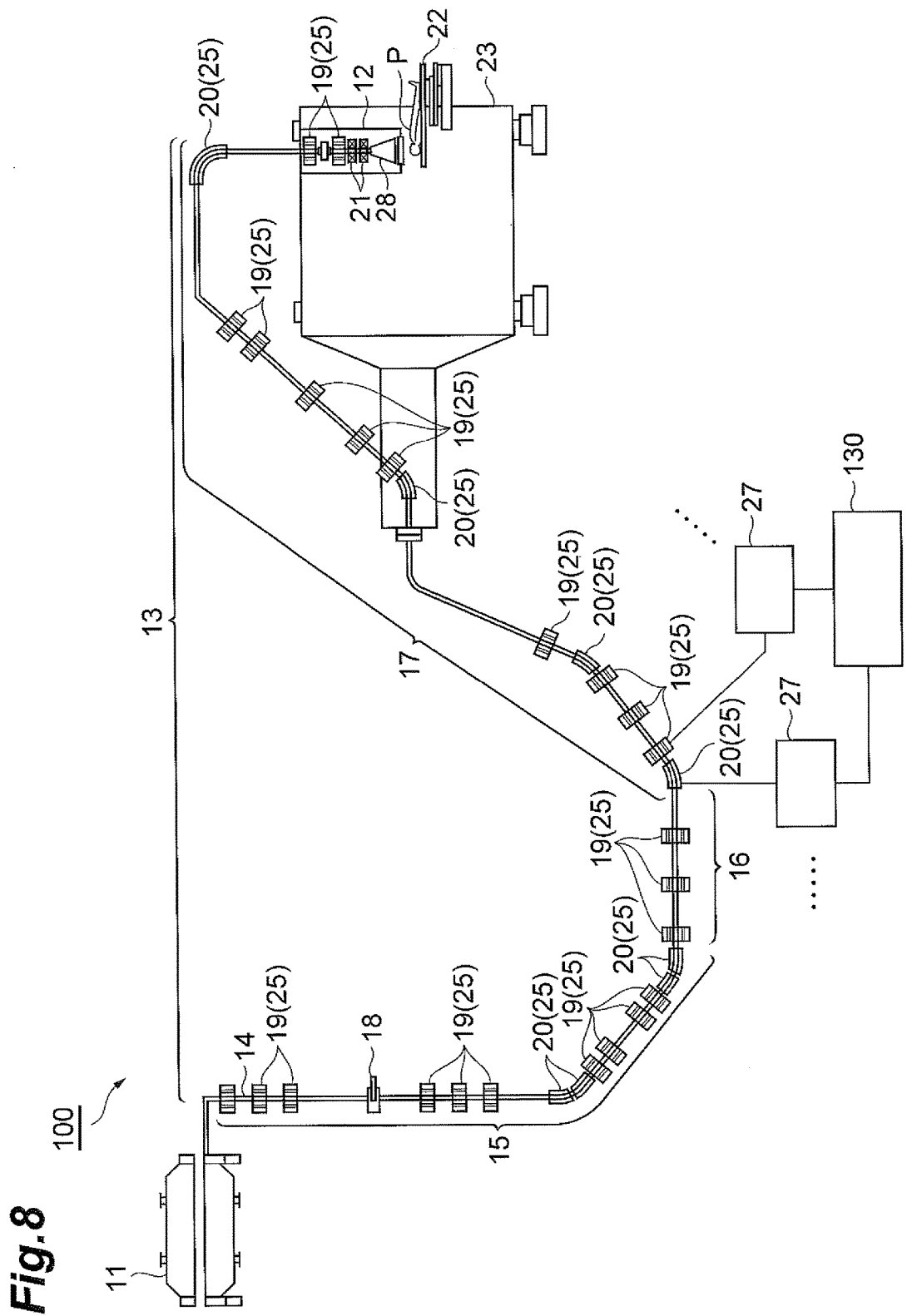
FIG. 8 is a schematic diagram illustrating a charged-particle beam irradiation device according to an embodiment of the invention.

A technique for setting the sum of the irradiation interruption times to be shorter than the sum of the irradiation times during one treatment is not limited to the technique for reducing the transmission time of the signal to the electromagnet as in the charged-particle beam therapy apparatus 1. For example, a technique for reducing the time until the energy of the electromagnet is consumed may be used. As a specific example, as illustrated in FIG. 8, a charged-particle beam therapy apparatus 100 is used for a cancer treatment using a radiation therapy and includes an accelerator 11 that accelerates charged particles and emits a charged-particle beam, an irradiation nozzle 12 (irradiation unit) that irradiates an irradiated body with the charged-particle beam, a beam transport line 13 (transport line) that transports the charged-particle beam emitted from the accelerator 11 to the irradiation nozzle 12, a degrader (energy adjustment unit) 18 that is provided in the beam transport line 13 and reduces the energy of the charged-particle beam to adjust the range of the charged-particle beam, a plurality of electromagnets 25 that are provided in the irradiation nozzle 12 and the beam transport line 13, electromagnet power supplies 27 that are provided so as to correspond to the plurality of electromagnets 25, and a control unit 130 that controls the overall operation of the charged-particle beam therapy apparatus 100. In this embodiment, a cyclotron is used as the accelerator 11. However, the accelerator 11 is not limited to the cyclotron. For example, the accelerator 11 may be other generation sources that generate the charged-particle beam, such as a synchrotron, a synchrocyclotron, and a linear accelerator. The structure of the charged-particle beam therapy apparatus 100 illustrated in FIG. 8 is the same as that of the charged-particle beam therapy apparatus 100 illustrated in FIG. 1 except for the control unit 130 and thus the description thereof will not be repeated.

Figure 9:
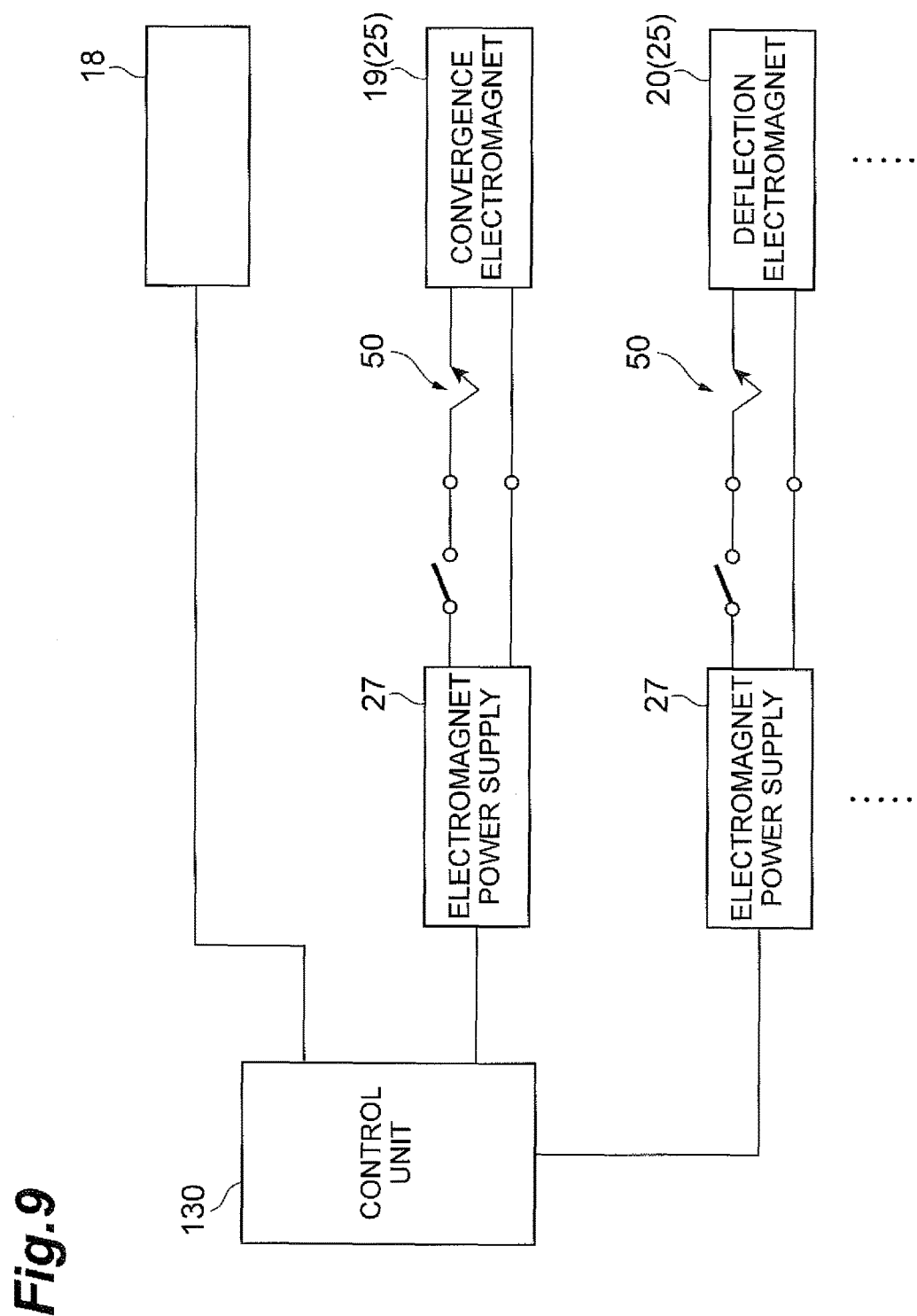
FIG. 9 is a block diagram illustrating the peripheral structure of a control unit and an electromagnet.

Next, the control unit 130 and the electromagnet power supplies 27 will be described in detail with reference to FIG. 9. In FIG. 9, only some of the electromagnet power supplies 27 are illustrated. However, in practice, the number of electromagnet power supplies 27 is equal to the number of electromagnets 25 provided in the charged-particle beam therapy apparatus 100.

The control unit 130 controls the irradiation of the irradiated body with the charged-particle beam emitted from the accelerator 11. The control unit 130 controls the scanning electromagnet 21 such that the charged-particle beam is radiated to the layer set in the irradiated body according to a predetermined scanning pattern. In addition, the control unit 130 controls the degrader 18 such that the energy of the charged-particle beam is adjusted and the range of the charged-particle beam is adjusted. In this way, the control unit 130 can switch the layer to which the charged-particle beam is radiated.

A semiconductor (transistor) 50 is connected in series between the electromagnet power supply 27 and the electromagnet 25. The control unit 130 controls the current input to the semiconductor 50 to control the resistance of the semiconductor 50. When the layer to which the charged-particle beam is radiated is switched, the control unit 130 controls the degrader 18 such that the energy of the charged-particle beam is reduced in order to shorten the range of the charged-particle beam. In this case, the control unit 130 reduces the current which is input from the electromagnet power supply 27 to the electromagnet 25, in order to reduce the amount of excitation of the electromagnet 25 in correspondence with the reduction in the energy of the charged-particle beam. In this case, the control unit 130 increases the resistance of the semiconductor 50 in order to absorb the remaining energy of the electromagnet 25.

Figure 10:
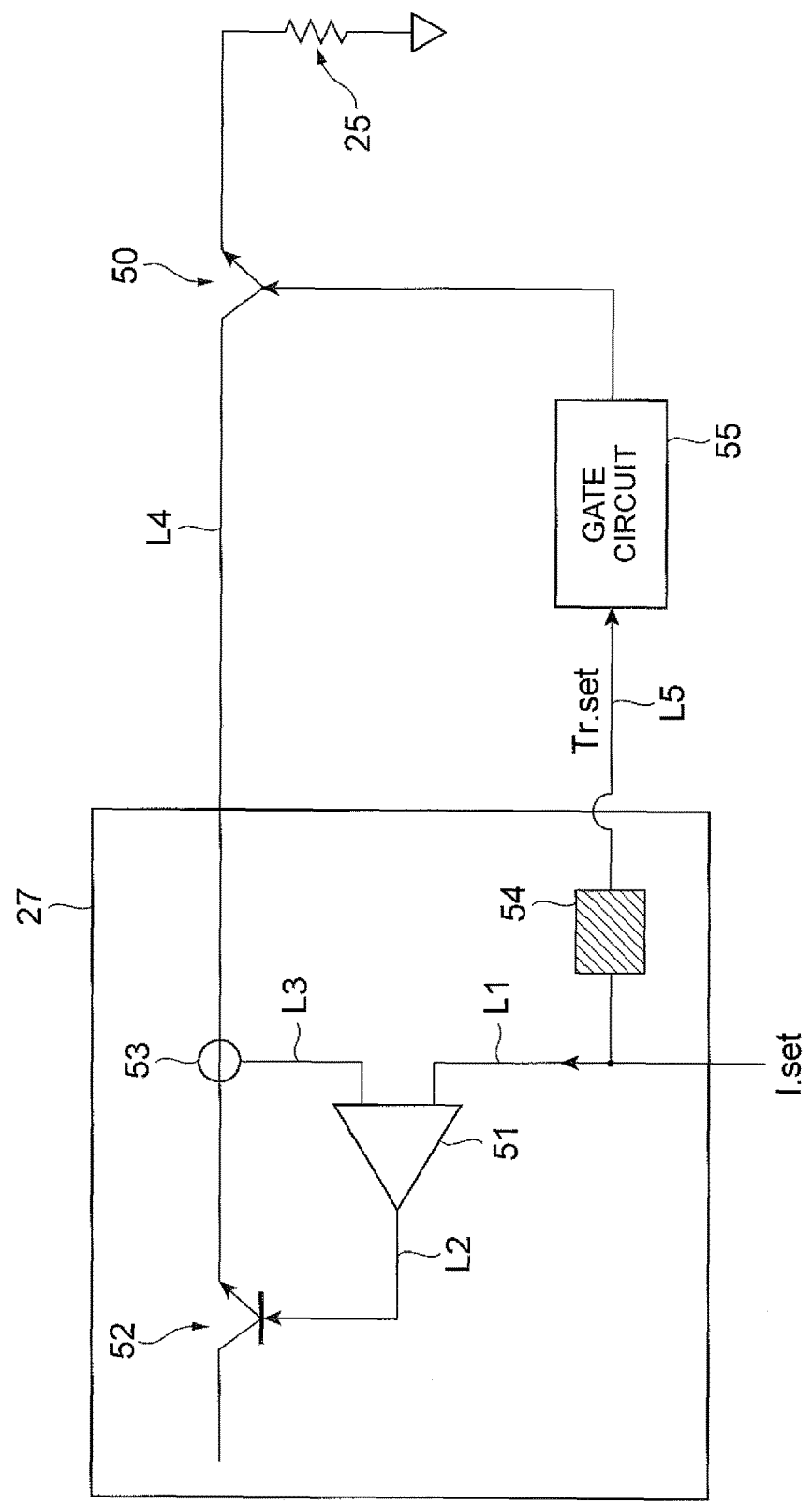
FIG. 10 is a diagram illustrating the structure of the peripheral circuit of an electromagnet power supply and a semiconductor.

Next, the structure of the peripheral circuit of the electromagnet power supply 27 and the semiconductor 50 will be described in detail with reference to FIG. 10. As illustrated in FIG. 10, in the electromagnet power supply 27, a current which is set to a current set value I.set passes through a line L1 and flows to a line L4 through a current feedback unit 51, a line L2, and a semiconductor 52. The semiconductor 50 is provided as a resistor in the line L4 and the current flows to the electromagnet 25 through the semiconductor 50. A current monitor 53 is provided in the line L4. The current monitor 53 detects a current and transmits a signal to the current feedback unit 51 through a line L3 to perform current feedback. A line L5 is branched from the line L1. A signal generation circuit 54 and a gate circuit 55 are provided in the line L5. The line L5 is connected to the semiconductor 50. In this circuit structure, when the current which is set to the current set value I.set flows through the line L1, the signal generation circuit 54 generates a signal which is set to a resistance set value Tr.set corresponding to the current set value I.set. The gate circuit 55 inputs a current corresponding to the resistance set value Tr.set to the semiconductor 50.

Figure 11:
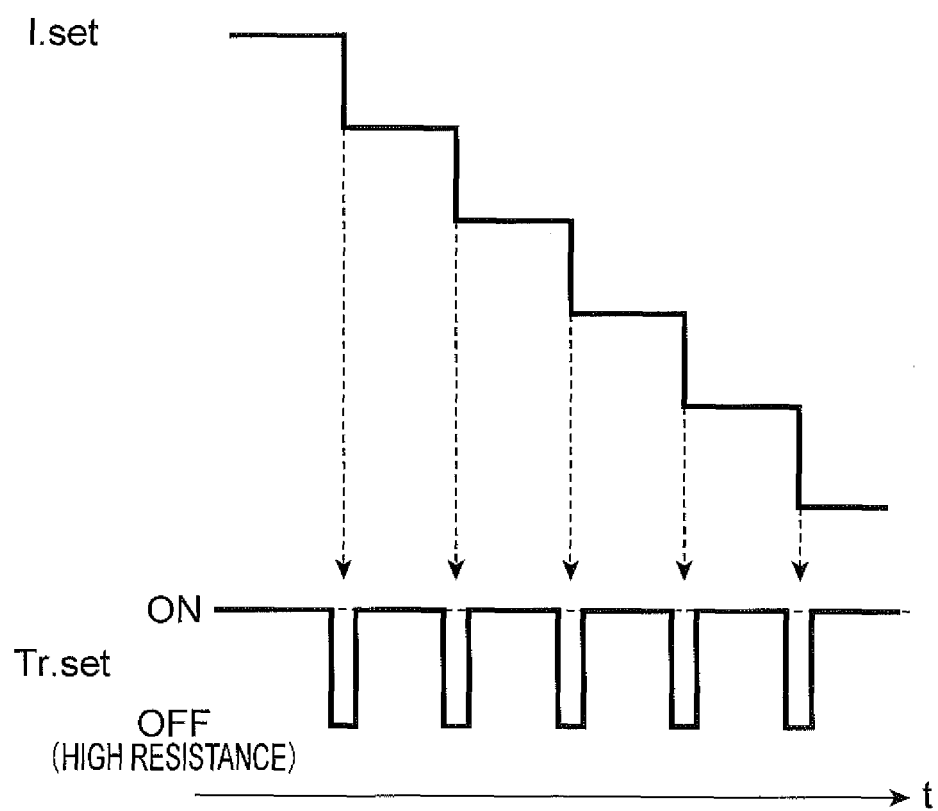
FIG. 11 is a conceptual diagram illustrating the relationship between a current which flows to the electromagnet and the resistance of the semiconductor.
Figure 12:
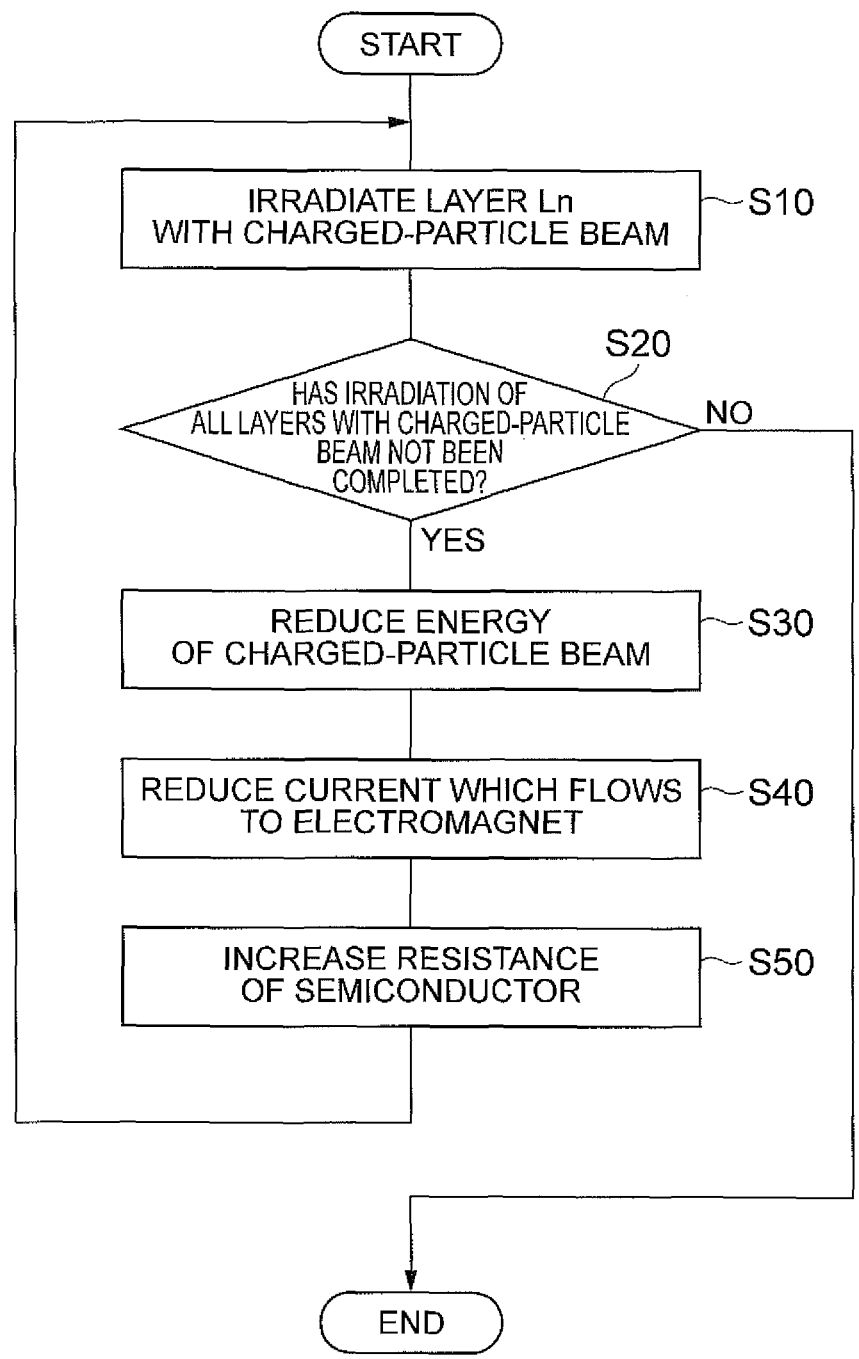
FIG. 12 is a flowchart illustrating the content of the process performed by the control unit of the charged-particle beam therapy apparatus.

Next, a method for adjusting the range of the charged-particle beam will be described with reference to FIGS. 11 and 12. FIG. 11 is a conceptual diagram illustrating the relationship between the current which flows to the electromagnet 25 and the resistance of the semiconductor 50. FIG. 12 is a flowchart illustrating the content of the process performed by the control unit 130 of the charged-particle beam therapy apparatus 100. As illustrated in FIG. 12, the control unit 130 controls the irradiation nozzle 12 such that the charged-particle beam is radiated to the layer $L_n$ according to the scanning pattern (Step S10). In this case, the control unit 130 controls the electromagnet power supply 27 such that a constant current (that is, the current set value I.set is constant) flows to the electromagnet 25 and sets the resistance set value Tr.set to an on state such that the semiconductor 50 has low resistance (see FIG. 11). Then, the control unit 130 determines whether the irradiation all of the layers $L_1$ to $L_N$ with the charged-particle beam has not been completed (Step S20). When it is determined that the irradiation with the charged-particle beam has not been completed, the control unit 130 performs the process of switching the layer to which the charged-particle beam is radiated.

Specifically, the control unit 130 controls the degrader 18 such that the energy of the charged-particle beam is reduced (Step S30). In addition, the control unit 130 controls the electromagnet power supply 27 such that the current set value I.set is reduced and the current which flows to the electromagnet 25 is reduced (Step S40). In this case, the control unit 130 sets the resistance set value Tr.set to an off state and increases the resistance of the semiconductor 50 (Step S50). Then, the semiconductor 50 absorbs the remaining energy of the electromagnet 25. As such, when the switching of the layer to be irradiated is repeated, the current set value I.set has a waveform in which it is reduced stepwise. In addition, the resistance set value Tr.set is set to an on state when the current set value I.set is set to a constant value and is locally set to an off state only when the current set value I.set is reduced. When the irradiation of all of the layers $L_1$ to $L_N$ with the charged-particle beam is completed, the determination result in S20 is "NO" and the process illustrated in FIG. 12 ends.

Next, the operation and effect of the charged-particle beam therapy apparatus 100 according to this embodiment will be described.

In the charged-particle beam therapy apparatus 100, when the layer of the irradiated body to which the charged-particle beam is radiated is switched, the control unit 130 controls the degrader 18 such that the energy of the charged-particle beam is reduced and the range of the charged-particle beam is shortened. In this case, since the energy of the charged-particle beam is reduced, the electromagnet power supply 27 needs to reduce the current which flows to the electromagnet 25 with the reduction in the energy. It is necessary to increase the time constant of the load in order to increase the rate of decrease of the current which flows to the electromagnet 25. Here, a structure is considered in which a resistor is provided in series between the electromagnet power supply 27 and the electromagnet 25 and the energy of the load (electromagnet 25) is consumed by the resistor. However, in this structure, the resistance of the resistor is very high and high resistance is applied even though it is not necessary (when the charged-particle beam is radiated). As a result, a large amount of power is needed. In addition, when a capacitor is provided in parallel between the electromagnet power supply 27 and the electromagnet 25 to recover the energy of the electromagnet 25, it is necessary to provide a capacitor with a very large size since the inductance of the electromagnet 25 is large.

In this embodiment, when the layer of the irradiated body to which the charged-particle beam is radiated is switched, the control unit 130 controls the degrader 18 such that the energy of the charged-particle beam is reduced and increases the resistance of the semiconductor 50 which is connected in series between the electromagnet power supply 27 and the electromagnet 25. The resistance of the semiconductor 50 is increased at the time when the current which flows to the electromagnet 25 is reduced to increase the time constant of the load. Therefore, it is possible to reduce the time required to reduce the current. That is, when the layer to which the charged-particle beam is radiated is switched, the switching time is reduced and it is possible to reduce the time required for a charged-particle beam therapy. For example, in the charged-particle beam therapy apparatus according to the related art, the time required to switch the layer is about 2 seconds. In contrast, in the charged-particle beam therapy apparatus 100 according to this embodiment, it is possible to switch the layer within about 100 milliseconds. In general, several tens of layers are provided. Therefore, it is possible to significantly reduce the sum of the layer switching times. As a result, it is possible to significantly reduce the time required for the charged-particle beam therapy. The control unit 130 can reduce the resistance of the semiconductor 50 at the time when it is not necessary to increase the resistance. Therefore, no problem occurs when the resistor or the capacitor is provided.

In the charged-particle beam therapy apparatus 100 according to this embodiment, the degrader 18 is provided between the accelerator 11 and the irradiation nozzle 12 and the electromagnets 25 include at least the convergence electromagnets 19 and the deflection electromagnets 20 which are provided in the beam transport line 13. Therefore, when the layer is switched, it is possible to reduce the time required to reduce the current which flows to the convergence electromagnet 19 or the deflection electromagnet 20.

The invention is not limited to the above-described embodiment. For example, the structure of the peripheral circuit of the electromagnet power supply is not limited to that illustrated in FIG. 10. The irradiation nozzle may be fixed, without using the rotating gantry 23, and fixed irradiation may be performed. In addition, in addition to the degrader 18, another degrader may be provided closer to the rotating gantry than to the cyclotron. The accelerator 11 may be a synchrotron and the degrader 18 may be provided in the accelerator 11.

Figure 13:
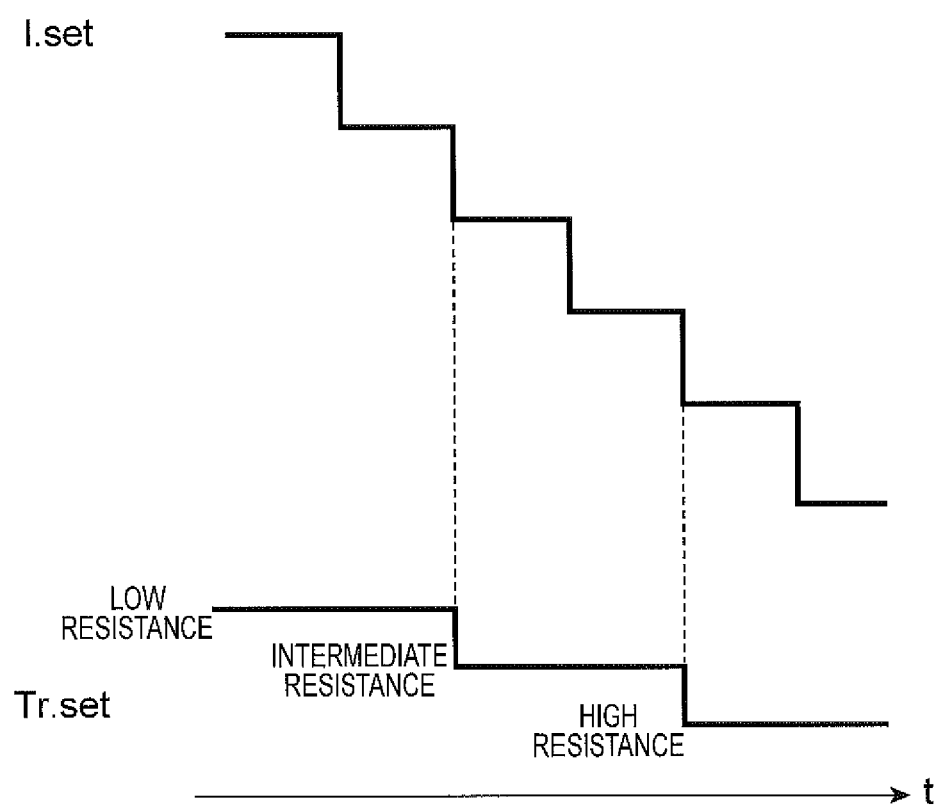
FIG. 13 is a conceptual diagram illustrating the relationship between the current which flows to the electromagnet and the resistance of the semiconductor.

The resistance pattern of the semiconductor 50 is not limited to that illustrated in FIG. 11. For example, the resistance pattern illustrated in FIG. 13 may be used. As illustrated in FIG. 13, when a large amount of current flows to the electromagnet 25, the resistance of the semiconductor 50 may be reduced. The resistance of the semiconductor 50 may be set to an intermediate value at the time when the current is reduced in several stages. The resistance of the semiconductor 50 may be set to a large value at the time when the current is further reduced in several stages.

The charged-particle beam therapy apparatus 100 illustrated in FIG. 8 can have the same operation and effect as the charged-particle beam therapy apparatus 1 illustrated in FIG. 1. That is, in the control pattern during one treatment which is stored in the control unit 130, the sum of the irradiation interruption times (here, the sum of the irradiation interruption times t2 for the switching process) for which the radiation of the charged-particle beam by the irradiation nozzle 12 is interrupted is set to be shorter than the sum of the irradiation times (the sum of the irradiation times t1) for which the charged-particle beam is radiated by the irradiation nozzle 12. As such, since the sum of the irradiation interruption times is set to be shorter than the sum of the irradiation times during one treatment, it is possible to reduce the total time required for one treatment. Therefore, the charged-particle beam therapy apparatus 1 can complete a treatment while the patient holds a breath and reduce the burden of patient during treatment.

In the charged-particle beam therapy apparatus 100 according to this embodiment, the control unit 130 alternately repeats the irradiation process of radiating the charged-particle beam to one layer set in the irradiated body and the switching process of switching the irradiation target to the next layer. In the control pattern, the irradiation time t1 is set to each irradiation process, the irradiation interruption time t2 is set to each switching process, and the irradiation time t1 for each irradiation process and the irradiation interruption time t2 for each switching process are continuously set. As such, in the control pattern, the irradiation time t1 for the irradiation process and the irradiation interruption time t2 for the switching process are alternately and continuously set. That is, the time for which the patient gets his or her breath back does not need to be ensured during each process and the charged-particle beam is radiated to the next layer immediately after the switching of the layer is completed. Therefore, it is possible to reduce the treatment time.

In the charged-particle beam therapy apparatus 100 according to this embodiment, the irradiation nozzle 12 can complete the irradiation of all of the layers set in the irradiated body with the charged-particle beam within 10 seconds. Therefore, it is possible to complete a treatment while the patient holds a breath and to reduce the burden of the patient during treatment.

In the embodiment of the invention, a method for reducing the time required for one treatment is not limited to that described with reference to FIG. 1 or FIG. 8. For example, in the process of switching the layer of the irradiated body, the switching speed of the degrader may increase (the rotational speed of a motor used to move the degrader increases to move the degrader at high speed) to reduce the irradiation interruption time.

It should be understood that the invention is not limited to the above-described embodiment, but may be modified into various forms on the basis of the spirit of the invention. Additionally, the modifications are included in the scope of the invention.

What is claimed is:

1. A charged-particle beam therapy apparatus irradiating with a charged-particle beam an irradiated body that is virtually sliced into a plurality of layers using a scanning method on each layer in an order, the charged-particle beam therapy apparatus comprising:
    an accelerator configured to accelerate a charged particle and emit the charged-particle beam;
    an irradiation unit configured to irradiate an irradiated body with the charged-particle beam using the scanning method; and
    a control unit, wherein
    the control unit stores a control pattern of the apparatus during one treatment,
    an irradiation interruption time for switching an irradiation target layer during which the irradiation of the irradiated body with the charged-particle beam from the irradiation unit is interrupted, and an irradiation time during which the irradiation unit irradiates the irradiated body with the charged-particle beam are set in the control pattern, the sum of the irradiation interruption times during one treatment is set to be shorter than the sum of the irradiation times during one treatment, the control unit alternately repeats an irradiation process of radiating the charged-particle beam to one layer set in the irradiated body and a switching process of switching an irradiation target to the next layer, in the control pattern, the irradiation time is set to each irradiation process and the irradiation interruption time is set to each switching process, and the irradiation time set to each irradiation process and the irradiation interruption time set to each switching process are set so that the charged-particle beam is radiated to the next layer immediately after the switching of the layer is completed.

2. The charged-particle beam therapy apparatus according to claim 1, wherein the irradiation unit is capable of completing the irradiation of all layers set in the irradiated body with the charged-particle beam within 10 seconds.

3. A method for controlling a charged-particle beam therapy apparatus including an irradiation unit which irradiates with a charged-particle beam an irradiated body that is virtually sliced into a plurality of layers using a scanning method on each layer in an order, and a control unit, the method comprising:

causing the control unit to control the irradiation of the irradiated body with the charged-particle beam on the basis of a control pattern of the apparatus during one treatment;

setting an irradiation interruption time for switching an irradiation target layer during which the irradiation of the irradiated body with the charged-particle beam from the irradiation unit is interrupted, and an irradiation time during which the irradiation unit irradiates the irradiated body with the charged-particle beam in the control pattern;

setting the sum of the irradiation interruption times during one treatment to be shorter than the sum of the irradiation times during one treatment; and causing the irradiation unit to irradiate the irradiated body with a charged-particle beam, wherein the control unit alternately repeats an irradiation process of radiating the charged-particle beam to one layer set in the irradiated body and a switching process of switching an irradiation target to the next layer, in the control pattern, the irradiation time is set to each irradiation process and the irradiation interruption time is set to each switching process, and the irradiation time set to each irradiation process and the irradiation interruption time set to each switching process are set so that the charged-particle beam is radiated to the next layer immediately after the switching of the layer is completed.

* * * * *